(12) United States Patent
Lavash

(10) Patent No.: US 8,808,264 B2
(45) Date of Patent: Aug. 19, 2014

(54) SANITARY NAPKIN FOR DYNAMIC BODY FIT

(75) Inventor: Bruce William Lavash, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/566,671

(22) Filed: Aug. 3, 2012

(65) Prior Publication Data

US 2012/0302984 A1    Nov. 29, 2012

Related U.S. Application Data

(63) Continuation of application No. 10/613,296, filed on Jul. 3, 2003, now Pat. No. 8,246,593.

(51) Int. Cl.
 *A61F 13/15* (2006.01)
(52) U.S. Cl.
 USPC ............ 604/385.16; 604/385.24; 604/385.26; 604/385.28; 604/385.22; 604/385.11; 604/378
(58) Field of Classification Search
 USPC ............ 604/385.16, 385.01, 385.24, 385.26, 604/385.28, 385.22, 385.11, 378
 See application file for complete search history.

(56) References Cited

U.S. PATENT DOCUMENTS

| | | | |
|---|---|---|---|
| 4,182,234 A | 1/1980 | Reed | |
| 4,804,380 A | 2/1989 | Lassen | |
| 5,007,906 A | 4/1991 | Osborn | |
| 5,324,278 A | 6/1994 | Visscher | |
| 5,454,802 A | 10/1995 | Lindquist | |
| 5,484,430 A | 1/1996 | Osborn | |
| 5,514,104 A | 5/1996 | Cole | |
| 5,558,656 A | 9/1996 | Bergman | |
| 5,611,790 A | 3/1997 | Sugahara et al. | |
| 5,624,421 A | 4/1997 | Dabi | |
| 5,674,214 A | 10/1997 | Visscher | |
| 5,702,382 A | 12/1997 | Osborn | |
| 5,713,883 A | 2/1998 | Hsieh | |

(Continued)

FOREIGN PATENT DOCUMENTS

| | | |
|---|---|---|
| EP | 0 888 765 A1 | 1/1999 |
| WO | WO 92/10984 A1 | 7/1992 |

(Continued)

OTHER PUBLICATIONS

PCT International Search Report dated Nov. 22, 2004.

(Continued)

*Primary Examiner* — Jacqueline F. Stephens
(74) *Attorney, Agent, or Firm* — George H. Leal; Megan C. Hymore; Andrew J. Hagerty

(57) ABSTRACT

An absorbent article providing improved body fit. The absorbent article includes an extensible fluid permeable facing layer and a first absorbent layer joined to the facing layer. Each zone of extensibility is a region of the first absorbent layer of relatively higher extensibility than regions of first absorbent layer adjacent to the zone of extensibility. A liquid impermeable backsheet is joined to the facing layer at the periphery. The liquid impermeable backsheet has a garment facing surface. A fastening means is disposed on at least a portion of the garment facing surface of the liquid impermeable backsheet. The fastening means defines attachment zones. At least a portion of the first absorbent layer is decoupled from the attachment zones of the fluid impermeable backsheet.

7 Claims, 3 Drawing Sheets

(56) References Cited

U.S. PATENT DOCUMENTS

| | | |
|---|---|---|
| 5,713,884 A | 2/1998 | Osborn |
| 5,824,004 A | 10/1998 | Osborn |
| 5,951,536 A | 9/1999 | Osborn |
| 6,059,764 A | 5/2000 | Osborn |
| 6,096,017 A | 8/2000 | Osborn |
| 6,221,062 B1 | 4/2001 | Osborn |
| 6,264,641 B1 | 7/2001 | Van Gompel |
| 6,287,288 B1 | 9/2001 | Osborn |
| 6,296,628 B1 | 10/2001 | Mizutani |
| 6,312,416 B1 | 11/2001 | Brisebois |
| 6,409,883 B1 | 6/2002 | Makolin |
| 6,423,045 B1 | 7/2002 | Wise |
| 6,447,494 B1 | 9/2002 | Kashiwagi |
| 6,448,466 B1 | 9/2002 | Carvalho |
| 6,450,999 B1 | 9/2002 | Kitabjian |
| 6,458,113 B2 | 10/2002 | Kashiwagi |
| 6,475,199 B1 | 11/2002 | Gann |
| 6,503,233 B1 | 1/2003 | Chen |
| 6,503,234 B1 | 1/2003 | Canuel |
| 6,562,192 B1 | 5/2003 | Hamilton |
| 6,585,712 B2 | 7/2003 | Yoshimasa |
| 6,695,827 B2 | 2/2004 | Chen |
| 2002/0055726 A1 | 5/2002 | Costa |
| 2003/0097105 A1 | 5/2003 | Chen |
| 2004/0147892 A1 | 7/2004 | Mizutani |
| 2004/0147893 A1 | 7/2004 | Mizutani |
| 2004/0147894 A1 | 7/2004 | Mizutani et al. |
| 2004/0147895 A1 | 7/2004 | Mizutani et al. |
| 2004/0147896 A1 | 7/2004 | Mizutani et al. |
| 2004/0147897 A1 | 7/2004 | Mizutani et al. |
| 2004/0147898 A1 | 7/2004 | Mizutani et al. |
| 2004/0149613 A1 | 8/2004 | Mizutani et al. |
| 2004/0153042 A1 | 8/2004 | Mizutani et al. |
| 2004/0158219 A1 | 8/2004 | Mizutani et al. |
| 2004/0158220 A1 | 8/2004 | Mizutani et al. |
| 2004/0158221 A1 | 8/2004 | Mizutani et al. |
| 2004/0158222 A1 | 8/2004 | Mizutani et al. |
| 2004/0158223 A1 | 8/2004 | Mizutani et al. |
| 2004/0162539 A1 | 8/2004 | Mizutani et al. |
| 2004/0167491 A1 | 8/2004 | Mizutani |
| 2004/0167492 A1 | 8/2004 | Mizutani et al. |
| 2004/0178104 A1 | 9/2004 | Mizutani et al. |
| 2004/0181201 A1 | 9/2004 | Mizutani et al. |
| 2005/0143597 A1 | 6/2005 | Mizushima et al. |

FOREIGN PATENT DOCUMENTS

| | | |
|---|---|---|
| WO | WO 95/17150 A2 | 6/1995 |
| WO | WO 95/20931 A1 | 8/1995 |
| WO | WO 97/01996 A1 | 1/1997 |
| WO | WO 98/27910 A1 | 7/1998 |
| WO | WO 98/27915 A1 | 7/1998 |
| WO | WO 98/55065 A1 | 10/1998 |
| WO | WO 99/01097 A1 | 1/1999 |
| WO | WO 02/36057 A1 | 5/2002 |

OTHER PUBLICATIONS

U.S. Appl. No. 10/613,296 (aka 9322), filed Jul. 3, 2003, Office Actions and Responses from Jul. 3, 2003 to Aug. 1, 2012.

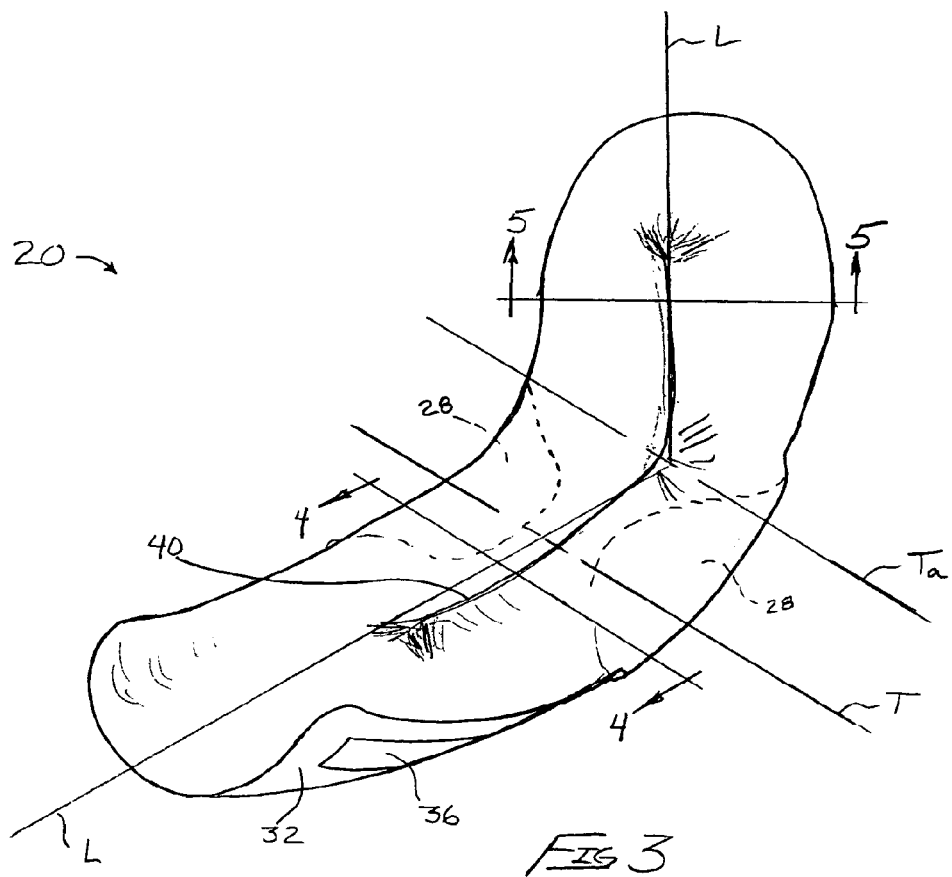
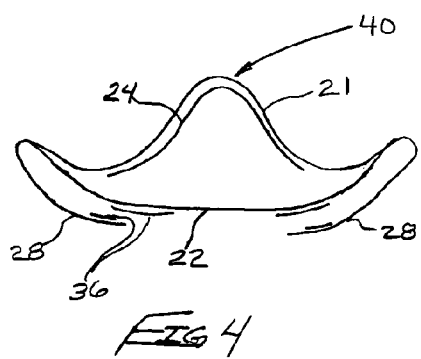
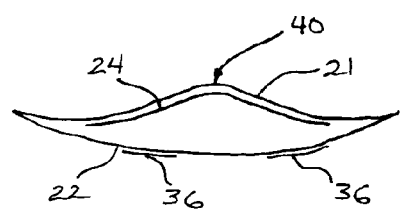

SANITARY NAPKIN FOR DYNAMIC BODY FIT

FIELD OF INVENTION

This invention relates to absorbent articles such as catamenial devices and light incontinence products. In particular, this invention relates to catamenial devices such as sanitary napkins having improved comfort and body fit.

BACKGROUND OF THE INVENTION

Sanitary napkins and related disposable absorbent articles that provide for the collection of menses and other bodily discharges are well known in the art. It has long been an object of those designing sanitary napkins to make them such that they readily intercept menses upon discharge from the wearer. Such sanitary napkins have long had a means, typically pressure sensitive adhesive, for affixing the sanitary napkin to the undergarment of the wearer and maintaining the sanitary napkin in the proper position to intercept the discharged menses.

However, the undergarment may not, in fact, move in concert with the body of the wearer. Specifically, the crotch of the undergarment of the wearer may not remain in constant registration with and position relative to the vaginal opening. Also, as the wearer walks, runs, sits, etc., the sanitary napkin may not flex and twist with the undergarment, thereby stressing the means for affixing the sanitary napkin to the undergarment of the wearer. In fact, the sanitary napkin may be detached from the undergarment.

Several attempts have been made to provide a sanitary napkin which may be attached to the undergarment of the wearer and also maintain the constant position with respect to the body of the wearer. For example, U.S. Pat. No. 4,425,130 issued Jan. 10, 1984 to DesMarais discloses a sanitary napkin having decoupled components joined to one another at the transverse or end edges.

Other attempts have been made in the art to provide a sanitary napkin which maintains contact of the topsheet with the body of the wearer. For example, U.S. Pat. No. 4,804,380, issued Feb. 4, 1989 to Lassen et al. discloses a three dimensionally shaped sanitary protecting device that claims to readily fit and align itself with the wearer's anatomy. However, the structure of Lassen does not provide the aforementioned independence of movement between the body of the wearer and the undergarment.

U.S. Pat. No. 5,007,906 issued Apr. 16, 1991 to Osborn, III et al. discloses a sanitary napkin having a topsheet and an absorbent core. The topsheet and core are decoupled from the backsheet of the sanitary napkin allowing the topsheet and backsheet to be separated from one another in the Z-direction. However, the decoupled topsheet and core of Osborn does not provide the desired body conformance.

Accordingly, there is a need for a disposable absorbent article having improved body fit that can be simply and economically manufactured.

Additionally, there is a need for a sanitary napkin capable of reliably achieving an improved body-fitting profile.

SUMMARY OF THE INVENTION

An absorbent article providing improved body fit is disclosed. The absorbent article has a longitudinal axis and a periphery. The absorbent article includes an extensible fluid permeable facing layer and a first absorbent layer joined to the facing layer. The first absorbent layer includes zones of extensibility. Each zone of extensibility is a region of the first absorbent layer of relatively higher extensibility than regions of first absorbent layer adjacent to the zone of extensibility. A liquid impermeable backsheet is joined to the facing layer at the periphery. The liquid impermeable backsheet has a garment facing surface. A fastening means is disposed on at least a portion of the garment facing surface of the liquid impermeable backsheet. The fastening means defines attachment zones. At least a portion of the first absorbent layer is decoupled from the attachment zones of the fluid impermeable backsheet.

BRIEF DESCRIPTION OF THE DRAWINGS

FIG. 3 is a perspective view of a sanitary napkin of the present invention as it might appear in use.

FIG. 4 is cross sectional view of Section 4-4 of FIG. 3.

FIG. 5 is a cross sectional view of Section 5-5 of FIG. 3.

DETAILED DESCRIPTION OF THE INVENTION

Figure 1:
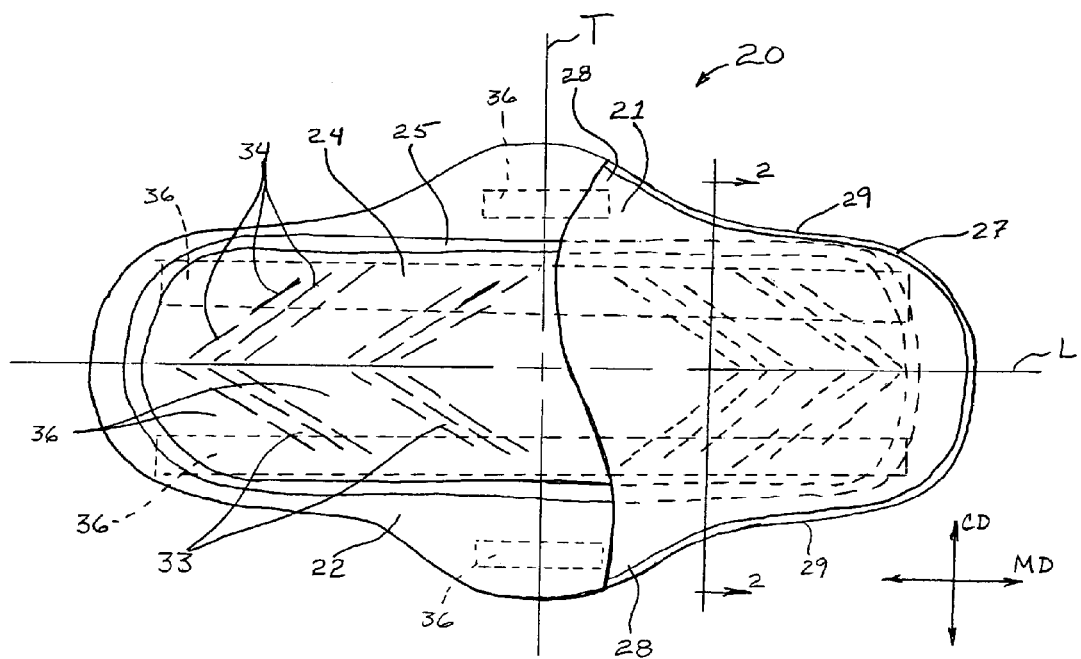
FIG. 1 is a plan view of a sanitary napkin of the present invention.

While the benefits of the present invention can be enjoyed in virtually all feminine hygiene products designed to be worn in the panties of the wearer, such as sanitary napkins, pantiliners, and light incontinence products, the invention will be disclosed with respect to the Figures as a preferred embodiment of a sanitary napkin.

The term "extensible," as used herein refers to webs or articles that, upon application of a force, can increase in at least one of their dimensions (e.g., in the MD-CD plane when in a substantially flat condition) sufficiently to permit three-dimensional deformation of the facing layer 21 and the first absorbent layer 24 for body fit and comfort, as discussed below. During use extensibility is preferably due to the naturally occurring forces imposed by the wearer's body and panties when the wearer uses the article of the present invention. The term extensible includes articles that are stretchable and elastically stretchable (defined below). Extensible materials or portions of materials, including in zones of extensibility referred to herein, preferably are extensible at least 5% under forces of less than or equal to about 800 grams, preferably less than or equal to about 400 grams, and most preferably less than or equal to about 300 grams.

The term "stretchable", as used herein, refers to articles that are extensible when stretching forces are applied to the article and offer some resistance to stretching.

As used herein the term "joined" refers to the condition where a first member is attached, or connected, to a second member either directly; or indirectly, where the first member is attached, or connected, to an intermediate member which in turn is attached, or connected, to the second member.

As used herein the term "decoupled" refers to the independence of movement of two components of the sanitary napkin 20 and requires separability of such components, at least within the range of movement experienced by the components during use.

As used herein, the term "nonwoven web" refers to a web having a structure of individual fibers or threads which are interlaid, but not in a regular, repeating manner as in a woven or knitted fabric. Nonwoven webs or fabrics have been formed from many processes, such as, for example, meltblowing processes, spunbonding processes, hydroentangling processes, and bonded carded web processes. The basis weight of nonwoven fabrics is usually expressed in grams per square meter (gsm) and the fiber diameters are usually expressed in microns. Fiber size can also be expressed in denier. The basis weight of nonwoven webs useful as components of the present invention, such as the facing layer 21 (which can be a single layer or a composite of more than one layer), can range from 10 gsm to 200 gsm.

The constituent fibers of nonwoven webs can be polymer fibers, and can be monocomponent, bicomponent, and/or biconstituent, capillary channel fibers, and can have major cross-sectional dimensions (e.g., diameter for round fibers) ranging from 5-200 microns. The constituent fibers can range from about 0.1 denier to about 100 denier.

As used herein, "spunbond fibers" refers to small diameter fibers that are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers that have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers that have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "capillary channel fibers" refers to fibers having capillary channels capable of facilitating fluid movement via capillarity. Such fibers can be hollow fibers, for example, but are preferably fibers having capillary channels on their outer surfaces. The capillary channels can be of various cross-sectional shapes such as "U-shaped," "H-shaped," "C-shaped," and "V-shaped."

FIG. 1 shows in partial cut away plan view one embodiment of a sanitary napkin 20 of the present invention comprising a fluid permeable facing layer 21, fluid impermeable backsheet 22, and a first absorbent layer 24 joined to the facing layer 21. Facing layer 21 and backsheet 22 can be joined about a periphery 27. Facing layer 21 of sanitary napkin 20 can be a body-contacting layer commonly known in the art as a topsheet 26. Facing layer 21 can be a composite comprising a topsheet 26 and a second absorbent layer, not shown in FIG. 1, also as known in the art. An optional second absorbent layer 25 can be disposed between first absorbent layer 24 and backsheet 22. Second absorbent layer 25 can be joined to portions of first absorbent layer 21 and can underlie (e.g., be in an overlapping relationship) all or a portion of first absorbent layer 21.

The sanitary napkin 20, as well as each layer or component thereof can be described as having a "body facing" surface and a "garment facing" surface. As can be readily understood by considering the ultimate use for sanitary napkins, the body facing surfaces are the surfaces of the layers or components that are oriented closer to the body when in use, and the garment facing surfaces are the surfaces that are oriented closer to the undergarment of the user when in use. Therefore, for example, facing layer 21 has a body facing surface 30 (that can actually be a body contacting surface), and a garment facing surface 31 that is the surface that can be adhered to the underlying first absorbent layer 24. The garment facing surface 32 of the fluid impermeable backsheet 22 of a sanitary napkin, for example, is oriented closest to, and may contact, the wearer's panties in use (via adhesive attachment means, if used).

Figure 2:
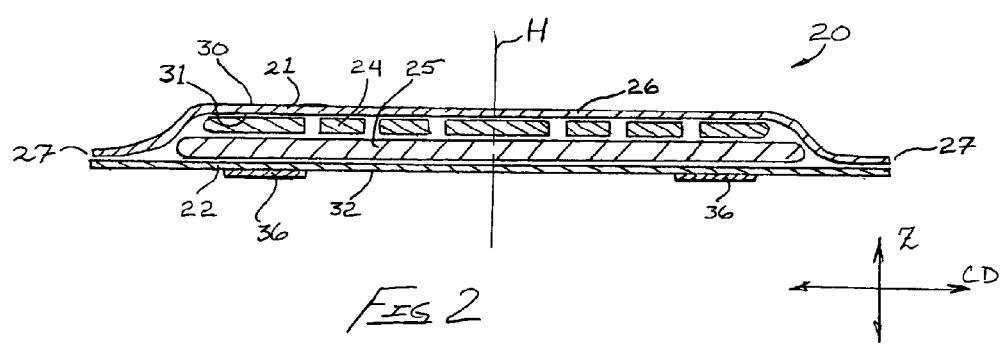
FIG. 2 is cross sectional view of Section 2-2 of FIG. 1.

Sanitary napkin 20 has a longitudinal axis L, a transverse axis T and a vertical axis H. Longitudinal axis L and transverse axis T define a two-dimensional plane of the sanitary napkin prior to use, which, in the embodiment shown is associated with the machine direction (MD) and cross machine direction (CD) as is commonly known in the art of making sanitary napkins in high-speed commercial production lines. The sanitary napkin 20 has a length, which is the longest dimension measured parallel to the longitudinal axis L. The sanitary napkin has a width, which is the dimension measured in the CD, e.g., parallel to the transverse axis. The width can vary or be substantially constant along the length of the sanitary napkin. In general, the width can be measured between lateral edges 29 parallel to the transverse axis T. Without being bound by theory, it is believed that the width should be sufficient to be effective in facilitating portions of the sanitary napkin to be deformed "out-of-plane," i.e., buckled, or deflected upwardly by the lateral, i.e., inward, compression forces of the wearer's thighs when the sanitary napkin is used. In general, by "out-of-plane" is meant extending in the "Z"-direction, as indicated by FIG. 2, and by "upward" is meant upward with respect to the orientation of FIGS. 2 and 3, which corresponds to the upward direction of a standing wearer of a sanitary napkin 20.

Sanitary napkin 20 can have side extensions 28, commonly referred to as "wings," designed to wrap the sides of the crotch region of the panties of the user of sanitary napkin 20. Sanitary napkin 20 and/or wings 28 can have fastening means including attachment components, such as pressure sensitive adhesive, or mechanical fasteners such as hook and loop fasteners. The sanitary napkin 20 shown in FIG. 1 has strips of positioning adhesive 36 on the garment facing surface 32 of backsheet 22. The positioning adhesive can be hot-melt adhesive material capable of establishing a temporary bond with the undergarment material. A suitable material is the composition designated HL-1491 XZP commercially available from H. B. Fuller, Toronto, Ontario, Canada. The fastening means can include attachment components such as positioning adhesive 36 disposed on the extensions 28, as shown in FIG. 1. The positioning adhesive, or other attachment components can be applied to the garment-facing surface of the backsheet in various patterns, including complete adhesive coverage, parallel longitudinal strips or lines, a line of adhesive following the perimeter of the structure, transverse lines of adhesive, or the like.

In general, the presence of fastening means defines an attachment zone that is coextensive with the fastening means. The attachment zone is the portion of the sanitary napkin, typically the backsheet thereof, that is fixed with respect to the wearer's panties. Thus, the attachment zone(s) must move in a one-to-one correspondence with the panty when the wearer moves. As discussed more fully below, one benefit of the present invention is a decoupling of the body-contacting portions of the sanitary napkin from the attachment zones. This decoupling improves body fit and comfort to the wearer of the sanitary napkin.

The sanitary napkin 20 can be made by hand or on commercial high-speed production lines as is known in the art.

To conform to the wearer's body, both statically and dynamically, the sanitary napkin must bend multi-axially, and the bending required is different at different locations along the longitudinal axis thereof. Moreover, to provide for increased body fit and comfort over longer periods of time, the sanitary napkin must be capable of adapting to the widely varying pudendal anatomies of different women, as well as the dynamically changing shape with their body movements during use. Body fit and comfort, both statically and dynamically, are provide for by the structure of the sanitary napkin of the present invention.

The sanitary napkin 20 of the present invention achieves improved static and dynamic body fit by providing zones of extensibility in the first absorbent layer wherein the zones of extensibility are decoupled from the attachment zones. As shown in FIG. 1, first absorbent layer 24 has at least one, and preferably a plurality of zones of extensibility 33. Zones of extensibility 33 are regions or portions of first absorbent layer that have been rendered relatively more easily extensible than adjacent, non-rendered regions so as to permit multi-axis bending of the absorbent layer 24. That is, for a given force applied to the sanitary napkin, such as by the wearer's body, portions of the sanitary napkin, e.g., the first absorbent layer 24, rendered more easily extensible will extend more than the adjacent, non-rendered portions of the sanitary napkin. Because the zones of extensibility are decoupled from the attachment zones, the zones of extensibility can move independently within the range of motion experienced by the sanitary napkin during use.

It is recognized that the forces applied to the sanitary napkin 20 of the present invention can be relatively low, such as the forces applied by the wearer's labia while walking Therefore, while it is recognized that all materials typically used in a sanitary napkin have some extensibility, the portions rendered extensible in the zones of extensibility 33 readily extend under the relatively low forces exerted by portions of the wearer's body for dynamic body fit and comfort. Another way of describing this property, therefore, is that the zones of extensibility 33 have a relatively lower elastic modulus, i.e., Young's modulus, than the adjacent non-rendered portions.

Extensibility can be rendered in the zones of extensibility 33 by means known in the art, such as by the method commonly referred to as "ring rolling" in which the portion to be rendered extensible is processed through the nip of counter-rotating, grooved rollers to locally incrementally stretch the rendered portion. Such methods are disclosed, for example, in U.S. Pat. Nos. 5,916,661 and 5,628,097. Likewise, extensibility can be rendered by similar means in which one of the counter-rotating rollers comprises teeth to form regions of extensibility comprising a plurality of spaced-apart rib-like elements, as disclosed in U.S. Pat. No. 5,518,801.

In a preferred embodiment, as shown in FIGS. 1 and 2, extensibility is rendered at predetermined zones of extensibility 33 by a plurality of openings defining slits 34 that permit extension of first absorbent layer 24 in at least one dimension, i.e., along the MD and/or the CD direction, or a combination thereof, when in a flattened, pre-use condition. Slits 34 are preferably arranged in a repeating "brick" pattern, in which a plurality of slits are arranged in rows, the slits being offset from row to row. Additionally, slits 34 are preferably oriented obliquely to, and arranged symmetrically about, longitudinal axis L. Without being bound by theory, it is believed that by orienting generally linear patterns of slits 34 obliquely to the longitudinal axis L, such as in the V-shaped pattern symmetric about the longitudinal axis L shown in FIG. 1, that first absorbent layer 24 is better adapted for multi-axis bending when used in a sanitary napkin.

Such slits can permit multi-axis bending, such as simultaneous bending about the longitudinal axis L to form an inverted V-shape that can itself be bent about an axis parallel to transverse axis T as shown in FIG. 3, and/or about an axis parallel to vertical axis Z. Such multi-axis bending provides for better body fit and comfort, since first absorbent layer 24 (and facing layer 21 joined thereto) can form to the wearers body in three-dimensions about multiple axes, and move with the wearers body during movements such as walking or sitting. FIG. 3 shows a simplified representation of a sanitary napkin 20 of the present invention as it might look when worn in the panties of a wearer. The backsheet 32 is fastened in a temporarily fixed relationship to the panties (not shown). Extensions 28 are wrapped about the elasticated side edges of the crotch portion of the panties. In use the sanitary napkin 20 fits the curvature of the wearer's body by bending both about axes parallel to the longitudinal axis L, and about axes parallel to transverse axis T, such as representative parallel axis Ta shown in FIG. 3. Such bending, imposed by the forces of the wearer's body and panties, can cause typical sanitary napkins to become bunched, crumpled, or, as is known in the art, to "rope" which is to become twisted and bunched. However, as shown in FIG. 3, a sanitary napkin 20 of the present invention can bend and articulate about multiple axes due to the presence of zones of extensibility 33, which are decoupled from the zones of attachment, and are, therefore, decoupled from being forced to move with the wearer's undergarments within the range of movement experienced during wear.

As shown in FIG. 3, and in the simplified schematic representations of FIGS. 4 and 5, a sanitary napkin 20 of the present invention, when worn, is adapted to form a flattened or concave portion for positioning exterior of the clitoris and pubic mons and a rearward portion adapted to yield a raised peak 40 (also referred to herein as a hump or ridge) having a length and forming at least a portion of the pad into an inverted V shape for positioning in alignment with the creases of the perineum and buttocks. The raised hump or ridge 40 can form as a result of the lateral forces imposed by the wearer's thighs. Such a configuration can be described in cross-section as an inverted V-shape, or as a "W" shape as shown in FIG. 4. The improved body fit and comfort of the sanitary napkin 20 of the present invention is realized, however, by the ability of the hump or ridge 40 to articulate in a generally smooth, un-crumpled manner about axes parallel to either or both of the transverse axis T, or axis H. Of course, the folds and bends of sanitary napkin 20 can articulate about other axes, but, for simplicity of description, the articulation is described herein as being about the major axes of a three-dimensional orthogonal space.

As shown in FIGS. 4 and 5, a generally "inverted V-" or "W-shaped" cross-section of the facing layer 21 and first absorbent material 24 is maintained in portions of the sanitary napkin where the first absorbent layer is decoupled from at least the attachment zones defined by fastening adhesive 36. The facing layer 21 and first absorbent material 24 are joined at least at the portions of first absorbent material 24 intermediate extensible zones 33. Such joining permits the facing layer 21 and first absorbent material 24 to conform as a composite, so to speak, or as a unit, to the body. Moreover, because the inverted V-shaped ridge 40 can articulate in three dimensions, i.e., multi-axially, the sanitary napkin 20 of the present invention provides for increased dynamic body fit and comfort. For example, when worn, the inverted V-shaped ridge 40 can dispose portions of the facing layer 21 and first absorbent material 24 in the labial region to reside between the labia. During walking motions when slight side to side movement of the labia could cause discomfort, the articulation of the ridge 40 about axes parallel to the H axis permit the body-contacting portions of the sanitary napkin to move with the body, improving comfort, particularly over relatively long periods of time or during periods of increased activity.

The sanitary napkin, therefore, can be described as an absorbent article for absorption of human exudate comprising a liquid impermeable backsheet, an extensible fluid permeable facing layer and an absorbent layer therebetween, and comprising a front portion adapted to form a flattened or concave portion for positioning exterior of the clitoris and pubic mons and a rearward portion adapted to yield a raised peak having a length and forming the pad into an inverted V shape for positioning in alignment with the creases of the perineum and buttocks, and wherein the liquid impermeable backsheet, the extensible fluid permeable facing layer and the absorbent layer are adapted to permit the raised peak to multi-axially articulate.

The specific extensibility and modulus can be adjusted by adjusting the size and spacing of zones of extensibility 33, and the optimum design based on the size and configuration of sanitary napkin 20 can readily be determined by those skilled in the art. For typical materials used in sanitary napkins, zones of extensibility covering a total of from about 10% to about 50% of first absorbent layer 24 can be used and the zones of extensibility can be sized and spaced so as to have generally equally-sized non-extensible zones adjacent zones of extensibility. In one embodiment, in a sanitary napkin similar to that shown in FIG. 1, and measuring about 25 cm long, first absorbent layer 24 has four zones of extensibility 33, two on each side of transverse axis T. Each zone of extensibility comprises linear patterns of slits 34 in a symmetric V-shaped pattern as shown in FIG. 1, with each slit being about 1 cm long. Each zone of extensibility measures about 2 cm in the longitudinal direction, and is separated by a distance of about 2 cm from adjacent zones of extensibility 33.

Because zones of extensibility 33 can be formed by methods such as slitting that can be performed relatively easily at the high speeds necessary for commercial production, sanitary napkins 20 of the present invention provide improved body fit that can be simply and economically manufactured. By providing such an easily manufactured structure, the first absorbent layer 24 can be made flat, and yet be adaptable to conform to the body of the wearer by folding. Further, the folds or ridges formed by folding can also articulate about any of axes L, T, or H during wearing and movement by the user, so that an improved fitting sanitary napkin is achieved. Thus, in one embodiment, the invention can be described as a sanitary napkin having a generally flattened pre-use configuration that can be described as being in a plane defined by the L and T axes, in which, upon use, portions of the sanitary napkin dynamically conform to the wearer's body. By dynamically conform is meant that, upon being worn next to the body in a panty of the wearer, the sanitary napkin is adapted to form a longitudinally-aligned fold, e.g., an inverted V shaped fold 40 about longitudinal axis L, and, unlike prior art sanitary napkins, the longitudinally-aligned fold can itself articulate about axes parallel to either the transverse axis T or axis H.

Figure 6:
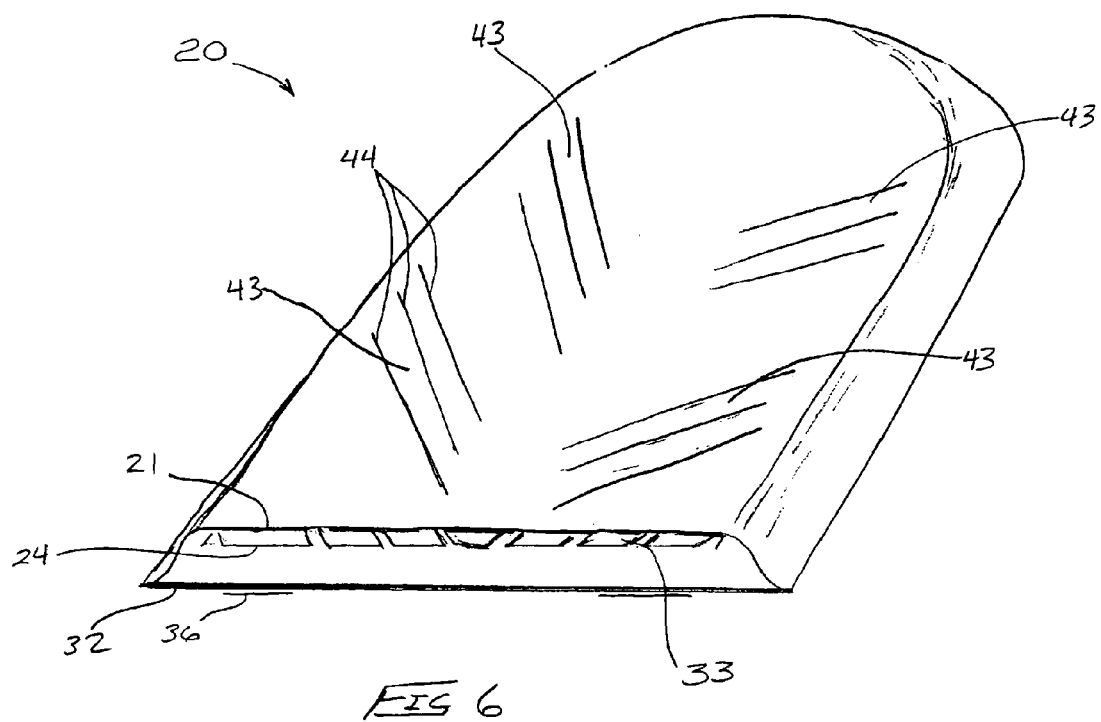
FIG. 6 is a partial perspective view of one embodiment of the present invention.

Facing layer 21 can comprise nonwoven materials or apertured polymer films as are known in the art for topsheets on disposable absorbent articles, and the facing layer can be extensible or have at least portions being extensible. For example, facing layer 21 can comprise an apertured polymer film sold under the trade name DRI-WEAVE® by The Procter & Gamble Co., Cincinnati, Ohio, or an apertured formed film as disclosed in U.S. Pat. No. 4,629,643, obtained from Tredegar Film Products, Terre Haute, Ind. under the designation X27121. If additional extensibility of facing layer 21 is desired, facing layer 21 or portions thereof can be rendered extensible. Portions to be zones of enhanced extensibility can be rendered extensible by the same methods described above with respect to rendering zones of extensibility in first absorbent layer 24. In general, since facing layer 21 and first absorbent layer 24 are bonded sufficiently to be, in effect, a laminate material, in a preferred embodiment facing layer 21 is sufficiently extensible, or rendered sufficiently extensible in zones of enhanced extensibility 43, as shown in FIG. 6. Zones of enhanced extensibility 43 can comprise, for example, embossments or debossments, such as raised ribs 44, aligned and spaced to complement the range of extensibility of the zones of extensibility 33 of first absorbent layer 24. In one embodiment, facing layer 21 and first absorbent layer 24 are joined, such as by adhesive or thermal bonding, such that the zones of enhanced extensibility 43 of facing layer 21 are in registry with, and, preferably, unbonded, i.e., not joined, to the zones of extensibility 33 of first absorbent layer 24.

First absorbent layer 24 (and second absorbent layer 25, if used), and backsheet 22 can comprise absorbent materials, and liquid impermeable film materials, respectively, as is well known in the art. Extensions 28, e.g., wings, if used, can be integral extensions of the facing layer or the backsheet or both, and they can be symmetric about the longitudinal axis L, transverse axis T, or both.

Nonwoven webs used in the present invention can be any known nonwoven webs or composites of two or more nonwoven webs. Nonwoven webs used in the present invention can comprise fibers that can be monocomponent, bicomponent, biconstituent, capillary channel fibers or combinations thereof. For use as the facing layer 21, nonwoven webs used in the present invention should be extensible.

Sanitary napkins of the present invention provide for improved body fit, as well as improved comfort, while absorbing all or most of any fluid discharges experienced by the wearer. These advantageous properties are a result of the shape the sanitary napkin takes on during use. Although provided in a generally flat configuration, upon use portions of a sanitary napkin of the present invention deform upwardly, i.e., toward the wearer's body, such that the body-facing surface of the napkin is in close proximity, or even in contact with, the wearer's body at the point of fluid discharge, thereby enhancing both the comfort of the wearer and the performance of the sanitary napkin. Moreover, an important improvement provided by the sanitary napkin 20 of the present invention is that the upwardly-deformed portion, e.g., ridge 40 can articulate about multiple axes under relatively low forces exerted by the wearer's body in the pudendal region, thereby permitting the sanitary napkin to dynamically conforming during use.

Joining of the facing layer 21 and the first absorbent layer 24 can be by any means known in the art, such as by adhesive bonding, thermal bonding, ultrasonic bonding, and the like. While complete bonding at interface is not necessary, or even desirable, it is believed that the bonding should be sufficient to facilitate the components act, as a unit, e.g., bending out-of-plane together. The facing layer 21 and first absorbent layer 24 can be joined, at least in portions intermediate zones of extensibility 33 by Findley HX1500-1 meltblown adhesive applied at a loading of approximately 6.4 gsm. Alternatively, the facing layer 21 and first absorbent layer 24 can be joined in selected regions by thermal bonding, for example, by thermal spot bonding.

First and/or second absorbent layer can be Foley Fluff pulp available from Buckeye Technologies Inc., Memphis, Tenn. that is disintegrated and formed into a core having a density of about 0.07 grams per cubic centimeter (g/cm$^3$) and a caliper of about 10 mm.

The extensibility and/or elastic modulus of portions of the components of sanitary napkin 20, including zones of extensibility 33 and zones of enhanced extensibility 43 is/are a property of materials that can be determined by any of many well-known means known in the art. In general, persons skilled in the art will recognize that any tensile test as are known and used in conjunction with testing equipment made by Instron, MTS, Thwing-Albert, and the like, can be used to measure stress/strain and to report extension and/or elastic modulus. It is implied herein that any of such tensile forces are measured at relatively low strains from about 0.1% to about 10%, and at appropriate rates of strain representative of in use conditions. By way of example, an appropriate rate of strain is defined as anything from 100% strain in about 2 seconds to 100% strain in about 3 minutes. For a given strain of between about 0.1% to about 10%, the ratio of the elastic modulus of the zones of extensibility 33 to the elastic modulus of the regions between (or intermediate to, or adjacent to; each term being synonymous in this context) the zones of extensibility 33 of first absorbent layer 24 can be from about 1 to 1.5 to about 1 to 1000, and is preferably from about 1 to 100 to about 1 to 300.

Joining of the facing layer 21 and the first absorbent layer 24 can be by any means known in the art, such as by adhesive bonding, thermal bonding, ultrasonic bonding, and the like. While complete bonding at interface is not necessary, it is believed that the bonding should be sufficient to facilitate the components act, as a unit, e.g., bending out-of-plane together upon sufficient lateral force, as described more fully below. In a preferred embodiment, the facing layer 21 is adhered to the body-facing side of the first absorbent layer 24 at substantially the entire surface interface between the two components, e.g., by the use of meltblown thermoplastic adhesive. Adhesion can be by application of a substantially uniform layer of adhesive applied by means known in the art, such as by spraying or slot coating. The adhesive, if uniformly coated should not block fluid flow into the first absorbent layer. Therefore, in a preferred embodiment, the adhesive is a fluid permeable adhesive, such as the aforementioned Findley HX1500-1 adhesive.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. An absorbent article having a longitudinal axis and a periphery, the absorbent article comprising:
    a. a fluid permeable facing layer, at least portions of which are extensible;
    b. a first absorbent layer joined to the facing layer, the first absorbent layer comprising a plurality of through openings;
    c. a liquid impermeable backsheet, at least portions of which are extensible, joined to the facing layer at the periphery, the liquid impermeable backsheet having a garment facing surface;
    d. a second absorbent layer joined to the backsheet, wherein a portion of the second absorbent layer exists below individual through openings in the first absorbent layer, and wherein a portion of the second absorbent layer is decoupled from the first absorbent layer;
    e. fastening means disposed on at least a portion of the garment facing surface of the liquid impermeable backsheet, the fastening means defining attachment zones; and
    f. wherein at least a portion of the first absorbent layer is decoupled from the attachment zones of the fluid impermeable backsheet.

2. The absorbent article of claim 1, wherein the first absorbent layer is substantially continuously joined to the facing layer.

3. The absorbent article of claim 1, wherein the facing layer has zones of enhanced extensibility.

4. The absorbent article of claim 1, wherein the facing layer comprises a topsheet and a secondary topsheet.

5. The absorbent article of claim 1, wherein the facing layer comprises an apertured, formed film.

6. The absorbent article of claim 1, wherein the facing layer comprises a nonwoven web.

7. The absorbent article of claim 1, wherein the absorbent article is a catamenial device.

* * * * *